US007648826B1

(12) United States Patent
Albertson et al.

(10) Patent No.: US 7,648,826 B1
(45) Date of Patent: Jan. 19, 2010

(54) **DETECTING *CYP24* EXPRESSION LEVEL AS A MARKER FOR PREDISPOSITION TO CANCER**

(75) Inventors: Donna G. Albertson, Lafayette, CA (US); Daniel Pinkel, Walnut Creek, CA (US); Colin Collins, San Raphael, CA (US); Joe W. Gray, San Francisco, CA (US); Bauke Ystra, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/285,292

(22) Filed: Apr. 2, 1999

(51) Int. Cl.
*C12Q 1/00* (2006.01)
*C12Q 1/68* (2006.01)
*C12Q 19/30* (2006.01)
*G01N 33/567* (2006.01)
*G01N 33/00* (2006.01)
*G01N 33/48* (2006.01)
*G01N 21/75* (2006.01)
*G01N 1/00* (2006.01)
*A61K 38/00* (2006.01)

(52) U.S. Cl. .............................. 435/7.23; 435/4; 435/6; 435/7.21; 435/7.92; 435/89; 435/91.1; 435/91.2; 436/63; 436/64; 436/86; 436/164; 436/166; 436/174; 530/300; 530/350; 536/18.7; 536/22.1; 536/23.1; 536/23.2; 536/23.5

(58) Field of Classification Search ..................... 435/4, 435/6, 7.21, 7.23, 89, 91.1, 91.2, 7.92; 436/174, 436/63, 64, 86, 164, 166; 530/300, 350; 536/18.7, 22.1, 23.1, 23.2, 23.5
See application file for complete search history.

(56) References Cited

FOREIGN PATENT DOCUMENTS

WO    WO 98/02539    1/1998

OTHER PUBLICATIONS

Tockman et al. Considerations in bringing a cancer biomarker to clinical application. Cancer Research (Suppl.) 52:2711s-2718s, May 1, 1992.*
Anzick et al., "AIB1, a Steroid Receptor Coactivator Amplified in Breast and Ovarian Cancer" *Science* (1997) 277:965-968.
Arbour et al., "A Highly Sensitive Method for Large-Scale Measurements of 1,25-Dihydroxyvitamin D" *Anal. Biochem.* (1998) 255:148-154.
Berger et al., "Immunocytochemical Detection of 1,25-Dihydroxyvitamin $D_3$ Receptor in Breast Cancer[1]" *Cancer Research* (1987) 47:6793-6799.
Buras et al., "Vitamin D receptors in breast cancer cells" *Breast Cancer Res. Treatment* (1994) 31:191-202.
Berns et al., "Oncogene amplification and prognosis in breast cancer: relationship with systemic treatment" *Gene* (1995) 11-18.
Borg et al., "ERBB2 amplification in breast cancer with a high rate of proliferation" *Oncogene* (1991) 6:137-143.
Borg et al., "*c-myc* Amplification is an Independent Prognostic Factor in Postmenopausal Breast Cancer" *Int. J. Cancer* (1992) 51:687-691.
Brinkmann et al., "The Human CAS (Cellular Apoptosis Susceptibility) Gene Mapping on Chromosome 20q13 Is Amplified in BT474 Breast Cancer Cells and Part of Aberrant Chromosomes in Breast and Colon Cancer Cell Lines" *Genome Res.* (1996) 6:187-194.
Collins et al., "Positional cloning of *ZNF217* and *NABC1*: Genes amplified at 20q13.2 and overexpressed in breast carcinoma" *Proc. Natl. Acad. Sci. USA* (1998) 95:8703-8708.
Colston et al., "Possible Role for Vitamin D. in Controlling Breast Cancer Cell Proliferation" *The Lancet* (1989) 188-191.
Courjal et al., "DNA amplifications at 20q13 and MDM2 define distinct subsets of evolved breast and ovarian tumors" *British Journal of Cancer* (1996) 74:1984-1989.
Eisman et al., "Suppression of in Vivo Growth of Human Cancer Solid Tumor Xenografts by 1,25-Dihydroxyvitamin $D_3$[1]" *Cancer Res.* (1987) 47:21-25.
Elstner et al., "20-epi-Vitamin $D_3$ Analogues: A Novel Class of Potent Inhibitors of Proliferation and Inducers of Differentiation of Human Breast Cancer Cell Lines[1]" *Cancer Research* (1995) 55:2822-2830.
Garland et al., "Geographic Variation in Breast Cancer Mortality in the United States: A Hypothesis Involving Exposure to Solar Radiation" *Preventive Medicine* (1990) 19:614-622.
Gaudray et al., "DNA amplification at 11q13 in human cancer: from complexity to perplexity" *Mutation Research* (1992) 276:317-328.
Gorham et al., "Acid Haze Air Pollution and Breast and Colon Cancer Mortality in 20 Canadian Cities" *Canadian Journal of Public Health* (1989) 80:96-100.
Gorham et al., "Sunlight and Breast Cancer Incidence in the USSR" *International Journal of Epidemiology* (1990) 19:820-824.
Isola et al., "Genetic Aberrations Detected by Comparative Genomic Hybridization Predict Outcome in Node-Negative Breast Cancer" *American Journal of Pathology* (1995) 147:905-911.
Iwabuchi et al., "Genetic Analysis of Benign, Low-Grade, and High-Grade Ovarian Tumors[1]" *Cancer Research* (1995) 55:6172-6180.
Kallioniemi et al., "Detection and mapping of amplified DNA sequences in breast cancer by comparative genomic hybridization" *Proc. Natl. Acad. Sci.* (1994) 91:2156-2160.

(Continued)

Primary Examiner—Alana M. Harris
(74) Attorney, Agent, or Firm—Weaver Austin Villeneuve & Sampson LLP; Emily M. Haliday

(57) ABSTRACT

This invention pertains to the discovery that an amplification of the CYP24 gene or an increase in CYP24 activity is a marker for the presence of, progression of, or predisposition to, a cancer (e.g., breast cancer). Using this information, this invention provides methods of detecting a predisposition to cancer in an animal. The methods involve (i) providing a biological sample from an animal (e.g. a human patient); (ii) detecting the level of CYP24 within the biological sample; and (iii) comparing the level of CYP24 with a level of CYP24 in a control sample taken from a normal, cancer-free tissue where an increased level of CYP24 in the biological sample compared to the level of CYP24 in the control sample indicates the presence of said cancer in said animal.

19 Claims, 3 Drawing Sheets

OTHER PUBLICATIONS

Love-Schimenti et al., "Antiestrogen Potentiation of Antiproliferative Effects of Vitamin $D_3$ Analogues in Breast Cancer Cells[1]" *Cancer Research* (1996) 56:2789-2794.

Mohapatra et al., "Detection of Multiple Gains and Losses of Genetic Material in ten Glioma Cell Lines by Comparative Genomic Hybridization" *Genes, Chromosomes & Cancer* (1995) 13-86-93.

Muleria et al., "Detection of DNA Amplification in 17 Primary Breast Carcinomas With Homogeneously Staining Regions by a Modified Comparative Genomic Hybridization Technique" *Genes, Chromosomes & Cancer* (1994) 10:160-170.

Reinhardt et al., "Ketoconazole Inhibits Self-Induced Metabolism of 1,25-Dihydroxyvitamin $D_3$ and Amplifies 1,25-Dihydroxyvitamin $D_3$ Receptor Up-Regulation in Rat Osteosarcoma Cells[1]" *Archives of Biochemistry and Biophysics* (1989) 272:459-465.

Reznikoff et al., "Long-term genome stability and minimal genotypic and phenotypic alterations in HPV16 E7-, but not E6-, immortalized human uroepithelial cells" *Genes & Development* (1994) 8:2227-2240.

Salvelieva et al., "20q gain associates with immortalization: 20q13.2 amplification correlates with genome instability in human papillomavirus 16 E7 transformed human uroepithelial cells" *Oncogene* (1997) 14:551-560.

Schlegel et al., "Comparative Genomic in Situ Hybridization of Colon Carcinomas with Replication Error[1]" *Cancer Research* (1995) 55:6002-6005.

Sen et al., "A putative serine/threonine kinase encoding gene *BTAK* on chromosome 20q13 is amplified and overexpressed in human breast cancer cell lines" *Oncogene* (1997) 14:2195-2200.

Simboli-Campbell et al., "Comparative effects of $1,25(OH)_2D_3$ and EB1089 on cell cycle kinetics and apoptosis in MCF-7 breast cancer cells" *Breast Cancer Research and Treatment* (1997) 42:31-41.

Solinas-Toldo et al., "Matrix-Based Comparative Genomic Hybridization: Biochips to Screen for Genomic Imbalances" *Genes, Chromosomes & Cancer* (1997) 20:399-407.

Solinas-Toldo et al., "Specific chromosomal imbalances in human papillomavirus-transfected cells during progression toward immortality" *Proc. Natl. Acad. Sci.* (1997) 94:3854-3859.

Stokke et al., "A physical Map of Chromosome 20 established Using Fluorescene in Situ Hybridization and Digital Image Analysis" *Genomics* (1995) 26:134-137.

Tanner et al., "Increased Copy No. at 20q13 in Breast Cancer: Defining the Critical Region and Exclusion of Candidate Genes[1]" *Cancer Research* 54:4257-4260.

Tanner et al., "Amplification of Chromosomal Region 20q13 in Invasive Breast Cancer: Prognostic Implications" *Clinical Cancer Research* (1995) 1:1455-1461.

Tanner et al., "Independent Amplification and Frequent Co-Amplification of Three Nonsyntenic Regions on the Long Arm of Chromosome 20 in Human Breast Cancer" *Cancer Research* (1996) 56:3441-3445.

Walters et al., "Newly Identified Action of the Vitamin D Endocrine System" *Endocrine Reviews* (1992) 13:719-764.

Williamson et al., "Chromosomal Mapping of the Human and Mouse Homologues of Two New Members of the AP-2 Family of Transcription Factors" *Genomics* (1996) 35:262-264.

Zhao et al., "Enhancement of Antiproliferative Activity of $1\alpha.25$-Dihydroxyvitamin $D_3$ (Analogs) by Cytochrome *P450* Enzyme Inhibitors is Compound- and Cell-type Specific" *J. Steroid Biochem. Molec. Biol.* (1996) 57:197-202.

Bockmühl et al., Genetisches Screening von Kopf-Hals-Karzinomen mittels der Komparativen Genomischen Hybridisierung (CGH), *Laryngo-Rhino-Otol* (1996) 75:408-414.

G. Jones et al., "Current Understanding of the Molecular Actions of Vitamin D" *Amer. Physiol. Soc.* (1998) 78:1193-1231.

Campbell et al. (1999) Molecular and Cellular Endocrinology 149, 169-183.

European Office Action dated Jul. 14, 2007 from corresponding European Application No. EP 00 916 145.6-2402.

International Search Report dated Jul. 24, 2000 issued in WO/2000/060109 (PCT/US2000/005972).

European Supplemental Search Report dated Jan. 3, 2005 issued in EP00916145.6.

European Office Action dated Feb. 8, 2006 issued in EP00916145.6.

Canadian Office Action dated May 15, 2008 issued in CA 2367291.

Armbrecht et al., "Insulin markedly potentiates the capacity of parathyroid hormone to increase expression of 25-hydroxvitamin D3-24-hydroxylase in rat osteoblastic cells in the presence of 1, 25-dihydroxyvitamin D3.", FEBS. 1996, vol. 393, pp. 77-80.

\* cited by examiner

DETECTING CYP24 EXPRESSION LEVEL AS A MARKER FOR PREDISPOSITION TO CANCER

STATEMENT AS TO RIGHTS TO INVENTIONS MADE UNDER FEDERALLY SPONSORED RESEARCH AND DEVELOPMENT

This invention was made with Government support under Grant No. CA 58207, awarded by the National Institutes of Health. The Government of the United States of America may have certain rights in this invention.

CROSS-REFERENCE TO RELATED APPLICATIONS

[Not Applicable]

FIELD OF THE INVENTION

This invention pertains to the field of cancer genetics and cytogenetics. In particular, this invention pertains to the identification of an association between amplification(s) of the CYP24 gene and cancer.

BACKGROUND OF THE INVENTION

Chromosome abnormalities are often associated with genetic disorders, degenerative diseases, and cancer. The deletion or multiplication of copies of whole chromosomes and the deletion or amplifications of chromosomal segments or specific regions are common occurrences in cancer (Smith (1991) Breast *Cancer Res. Treat.* 18: Suppl. 1:5-14; van de Vijer (1991) *Biochim. Biophys. Acta.* 1072:33-50). In fact, amplifications and deletions of DNA sequences can be the cause of a cancer. For example, proto-oncogenes and tumor-suppressor genes, respectively, are frequently characteristic of tumorigenesis (Dutrillaux (1990) *Cancer Genet. Cytogenet.* 49: 203-217). Clearly, the identification and cloning of specific genomic regions associated with cancer is crucial both to the study of tumorigenesis and in developing better means of diagnosis and prognosis.

Studies using comparative genomic hybridization (CGH) have revealed approximately twenty amplified genomic regions in human breast tumors (Muleris (1994) *Genes Chromosomes Cancer* 10:160-170; Kalliioniemi (1994) *Proc. Natl. Acad. Sci. USA* 91: 2156-2160; Isola (1995) *Am. J. Pathol.* 147:905-911). These regions are predicted to encode dominantly acting genes that may play a role in tumor progression or response to therapy. Three of these amplified regions have been associated with established oncogenes: ERBB2 at 17q12, MYC at 8q24 and CCND1 and EMS1 at 11q13. In breast cancer, ERBB2 and CCND1/EMS1 amplification and overexpression are associated with decreased life expectancy (Gaudray (1992) *Mutat. Res.* 276:317-328; Borg (1991) *Oncogene* 6:137-143). MYC amplification has been associated with lymph node involvement, advanced stage cancer and an increased rate of relapse (Borg (1992) *Intern. J. Cancer* 51: 687-691; Berns (1995) *Gene* 159: 11-18). Clearly, the identification of additional amplified genomic regions associated with breast cancer or other tumor cells is critical to the study of tumorigenesis and in the development of cancer diagnostics.

One of the amplified regions found in the CGH studies was on chromosome 20, specifically, 20q13. Amplification of 20q13 was subsequently found to occur in a variety of tumor types and to be associated with aggressive tumor behavior. Increased 20q13 copy number was found in 40% of breast cancer cell lines and 18% of primary breast tumors (Kalliioniemi (1994) supra). Copy number gains at 20q13 have also been reported in greater than 25% of cancers of the ovary (Iwabuchi (1995) *Cancer Res.* 55:6172-6180), colon (Schlegel (1995) *Cancer Res.* 55: 6002-6005), head-and-neck (Bockmuhl (1996) *Laryngor.* 75: 408-414), brain (Mohapatra (1995) *Genes Chromosomes Cancer* 13: 86-93), and pancreas (Solinas-Toldo (1996) *Genes Chromosomes Cancer* 20:399-407).

The 20q13 region was analyzed at higher resolution in breast tumors and cell lines using fluorescent in situ hybridization (FISH). A 1.5 megabase (Mb) wide amplified region within 20q13 was identified (Stokke (1995) *Genomics* 26: 134-137); Tanner (1994) *Cancer Res.* 54:4257-4260). Interphase FISH revealed low-level (>1.5x) and high level (>3x) 20q13 sequence amplification in 29% and 7% of breast cancers, respectively (Tanner (1995) *Clin. Cancer Res.* 1: 1455-1461). High level amplification was associated with an aggressive tumor phenotype (Tanner (1995) supra; Coujal (1996) *Br. J. Cancer* 74: 1984). Another study, using FISH to analyze 14 loci along chromosome 20q in 146 uncultured breast carcinomas, identified three independently amplified regions, including RMC20C001 region at 20q13.2 (highly amplified in 9.6% of the cases), PTPN1 region 3 Mb proximal (6.2%), and AIB3 region at 20q11 (6.2%) (Tanner (1996) *Cancer Res.* 56:3441-3445). Clearly, definitive characterization of amplified regions within 20q13 would be an important step in the diagnosis and prognosis of these cancers.

Increased copy number of chromosome 20q in cultured cells also has been associated with phenotypes characteristic of progressing tumors, including immortalization and genomic instability. For example, increased copy number at 20q11-qter has been observed frequently in human uro-epithelial cells (HUC) (Reznikoff (1994) *Genes Dev.* 8: 2227-2240) and keratinocytes (Solinas-Toldo (1997) *Proc. Natl. Acad. Sci. USA* 94:3854-3859) after transfection with human papilloma virus (HPV)16 E7 or HPV16, respectively. In addition, increased copy number at 20q13.2 has been associated with p53 independent genomic instability in some HPV16 E7 transfected HUC lines (Savelieva (1997) *Oncogene* 14: 551-560). These studies suggest that increased expression of one or more genes on 20q and especially at 20q13.2 contribute to the evolution of breast cancer and other solid tumors. Several candidate oncogenes have been identified as amplified on 20q, including AIB1 (Anzick (1997) *Science* 277: 965-968), BTAK (Sen (1997) *Oncogene* 14: 2195-200), CAS (Brinkmann (1996) *Genome Res.* 6: 187-194) and TFAP2C (Williamson (1996) *Genomics* 35:262-264). Clearly, definitive characterization of nucleic acid sequences in 20q13 associated with tumor phenotypes would be an important step in the diagnosis and prognosis of these cancers. The present invention fulfills these and other needs.

SUMMARY OF THE INVENTION

This invention pertains to the discovery that an amplification of the CYP24 gene or an increase in CYP24 activity is a marker for the presence of, progression of, or predisposition to, a cancer (e.g., breast cancer). Using this information, this invention provides methods of detecting/evaluating a predisposition to, progression of, or prognosis of cancer in an animal. Thus, in one embodiment, this invention provides methods of detecting a predisposition to cancer in an animal. The methods involve providing a biological sample from said animal, detecting the level of CYP24 within the biological sample; and comparing the level of CYP24 with a level of CYP24 in a control sample taken from a normal, cancer-free tissue;

where an increased level of CYP24 in the biological sample compared to the level of CYP24 in the control sample indicates the presence of a cancer in the animal. Similarly, an increased level of CYP24 in the sample can indicate a poor prognosis for an animal/patient known to have cancer, and/or a reduced survival expectancy, and/or the actual presence of a cancer.

In one embodiment, the level of CYP24 is detected by determining the copy number of CYP24 genes in the cells of the biological sample. In a particularly preferred embodiment, the copy number is measured using Comparative Genomic Hybridization (CGH). In another preferred embodiment, the copy number is determined by hybridization to an array of nucleic acid probes and in another particularly preferred embodiment, the Comparative Genomic Hybridization is performed on an array.

In another embodiment, the level of CYP24 is detected by measuring the level of CYP24 mRNA in the biological sample (e.g., by hybridization to one or more probes in an array), wherein an increased level of CYP24 RNA in said sample compared to CYP24 RNA in said control sample indicates a predisposition to cancer. In preferred embodiments, the level of CYP24 is measured in said biological sample and said control sample at the same vitamin D receptor activity or the CYP24 levels are normalized to the level of vitamin D receptor activity in the sample and control.

In still another embodiment, the level of CYP24 is detected by measuring the level of CYP24 protein in the biological sample, where an increased level of CYP24 protein in the sample as compared to CYP24 protein in said control sample indicates a predisposition to cancer. In preferred embodiments, the level of CYP24 protein is measured in the biological sample and the control sample at the same vitamin D receptor activity or the protein levels are normalized to the level of vitamin D receptor activity in the sample and control.

In still yet another embodiment, the level of CYP24 is detected by measuring the level of 25-hydroxyvitamin D3 24-hydroxylase enzyme activity in the biological sample, wherein an increased level of 25-hydroxyvitamin D3 24-hydroxylase enzyme activity in the sample as compared to 25-hydroxyvitamin D3 24-hydroxylase enzyme activity in the control sample indicates a predisposition to cancer. In preferred methods, the level of 25-hydroxyvitamin D3 24-hydroxylase activity is measured in the biological sample and the control sample at the same vitamin D receptor activity or the activity levels are normalized to the level of vitamin D receptor activity in the sample and control.

In the methods described herein, the animal(s) are mammals, more preferably mammals selected from the group of humans, non-human primates, canines, felines, murines, bovines, equines, porcines, and lagomorphs.

Preferred biological samples are selected from the group consisting of excised tissue (e.g., tissue biopsy), whole blood, serum, plasma, buccal scrape, saliva, cerebrospinal fluid, and urine.

In preferred embodiments, the difference between the increased level of CYP24 in the biological sample and the level of CYP24 in said control sample is a statistically significant difference (e.g. the increased level of CYP24 in the biological sample is at least about 2-fold greater, more preferably at least 4-fold greater than the level of CYP24 in the control sample).

This invention also provides methods of treating cancer in an animal. The methods involve performing the assays as described herein (e.g. providing a biological sample from said animal; detecting the level of CYP24 within said biological sample; and comparing said level of CYP24 with a level of CYP24 in a control sample from a normal, cancer-free tissue) and selecting and performing a cancer therapy in those animals having an increased level of CYP24 compared to the level of CYP24 in said control sample. In preferred embodiments, the cancer therapy is selected from the group consisting of chemotherapy, radiation therapy, surgery, antihormone therapy, and immunotherapy. In some preferred embodiments, the cancer therapy is an adjuvant cancer therapy.

This invention also provides methods of screening a test agent for the ability to inhibit proliferation of a CYP24-expressing cell. The methods involve contacting the CYP24-expressing cell with said test agent; and detecting the level of CYP24 activity, where a decreased level of CYP24 activity as compared to the level of CYP24 activity in a cell not contacted with the agent indicates that the agent inhibits proliferation of said cell. In a preferred embodiment, the cell is contacted with vitamin D. The detection of CYP24 level can be as described herein. In some embodiments the CYP24-expressing cell is a tumor cell. In some embodiments, the CYP24-expressing cell is a hyperproliferative cell. In particularly preferred embodiments, the difference between said decreased level of CYP24 activity and the level of CYP24 activity in a cell not contacted with said agent is a statistically significant difference (e.g. at least 2-fold lower, more preferably at least 4-fold lower in the cell contacted with the test agent).

This invention additionally provides methods of decreasing the proliferation of a cell with an elevated level of CYP24. The methods involve reducing the level of CYP24 activity in the cell using an inhibitor of CYP24. The methods can further involve contacting the cell with vitamin D. The cell can be a tumor cell (e.g., breast cancer cell, prostate cancer cell, colorectal cancer cell, leukemia cell, lymphoma, lung cancer cell, brain cancer cell, pancreatic cancer cell, colon cancer cell, and ovarian cancer cell). The cell can be a hyperproliferative cell. The cell can also be a metastatic cell. Preferred inhibitors include antisense oligonucleotides, ribozymes, repressors of CYP24 gene expression, competitive inhibitors of 25-hydroxyvitamin D3 24-hydroxylase activity, and noncompetitive inhibitors of 25-hydroxyvitamin D3 24-hydroxylase activity.

DEFINITIONS

To facilitate understanding the invention, a number of terms are defined below.

A "CYP24 gene" is a DNA sequence that encodes a 25'-hydroxyvitamin D3 24-hydroxylase enzyme (see, e.g. GenBank Accession Numbers U60669 S78775 and X59506). The term gene can refer to a mutated copy of the gene, or a fragment of the gene.

The term "VDR" refers to a vitamin D receptor.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt* 2, "*Overview of principles of hybridization and the strategy of nucleic acid probe assays*," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). A typical stringent wash for an array hybridization is 50% formamide, 2×SSC at 50° C. to 50° C. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "labeled with a detectable composition", as used herein, refers to a nucleic acid attached to a detectable composition, i.e., a label. The detection can be by, e.g., spectroscopic, photochemical, biochemical, immunochemical, physical or chemical means. For example, useful labels include $^{32}$P, $^{35}$S, $^{3}$H, $^{14}$C, $^{125}$I, $^{131}$I; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), calorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties (see, e.g., Mansfield (1995) *Mol Cell Probes* 9: 145-156). It will be appreciated that combinations of labels can also be used. Thus, for example, in some embodiments, different nucleic acids may be labeled with distinguishable (e.g. differently colored) labels.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompasses by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from CYP24. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 μm to about 3 mm, preferably between about 5 μm and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations. In various embodiments, target element sequences will have a complexity between about 1 kb and about 1 Mb, between about 10 kb to about 500 kb, between about 200 to about 500 kb, and from about 50 kb to about 150 kb.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. Particularly in the case of arrays, either probe or target nucleic acids may be affixed to the array. Whether the array comprises "probe" or "target" nucleic acids will be evident from the context. Similarly, depending on context, either the probe, the target, or both can be labeled. The probe is produced from a source of nucleic acids from one or more particular (preselected) portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The term "sample of human nucleic acid" as used herein refers to a sample comprising human DNA or RNA in a form suitable for detection by hybridization or amplification. The nucleic acid may be isolated, cloned or amplified; it may be, e.g., genomic DNA, mRNA, or cDNA from a particular chromosome, or selected sequences (e.g. particular promoters, genes, amplification or restriction fragments, cDNA, etc.) within particular amplicons or deletions disclosed here. The nucleic acid sample may be extracted from particular cells or tissues. The cell or tissue sample from which the nucleic acid sample is prepared is typically taken from a patient suspected of having cancer associated with the amplicon amplification or deletion or translocation being detected. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The sample may be isolated nucleic acids immobilized on a solid. In one embodiment, the sample may be prepared such that individual nucleic acids remain substantially intact and typically comprises interphase nuclei prepared according to standard techniques.

The phrase "detecting a cancer" refers to the ascertainment of the presence or absence of cancer in an animal. "Detecting a cancer" can also refer to obtaining indirect evidence regarding the likelihood of the presence of cancerous cells in the animal or to the likelihood or predilection to development of a cancer. Detecting a cancer can be accomplished using the methods of this invention alone, or in combination with other methods or in light of other information regarding the state of health of the animal.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, a melanoma, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, and a chondrosarcoma.

An "animal" refers to a member of the kingdom Animalia, characterized by multicellularity, the possession of a nervous system, voluntary movement, internal digestion, etc. An "animal" can be a human or other mammal. Preferred animals include humans, non-human primates, and other mammals. Thus, it will be recognized that the methods of this invention contemplate veterinary applications as well as medical applications directed to humans.

"Providing a biological sample" means to obtain a biological sample for use in the methods described in this invention. Most often, this will be done by removing a sample of cells from an animal, but can also be accomplished by using previously isolated cells (e.g. isolated by another person), or by performing the methods of the invention in vivo.

A "biological sample" refers to a cell or population of cells or a quantity of tissue or fluid from an animal. Most often, the sample has been removed from an animal, but the term "biological sample" can also refer to cells or tissue analyzed in vivo, i.e. without removal from the animal. Often, a "biological sample" will contain cells from the animal, but the term can also refer to non-cellular biological material, such as non-cellular fractions of blood, saliva, or urine, that can be used to measure CYP24 levels. Preferred biological samples include tissue biopsies, scrapes (e.g. buccal scrapes), whole blood, plasma, serum, urine, saliva, cell culture, or cerebrospinal fluid.

"Detecting a level of CYP24" refers to determining the number of CYP24 genes or the expression level of a gene or genes encoding 25-hydroxyvitamin D3 24-hydroxylase enzyme. The copy number of a gene can be measured in multiple ways known to those of skill in the art, including, but not limited to, Comparative Genomic Hybridization (CGH) and quantitative DNA amplification (e.g. quantitative PCR). Gene expression can be monitored in a variety of ways, including by detecting mRNA levels, protein levels, or protein activity, any of which can be measured using standard techniques. Detection can involve quantification of the level of CYP24 (e.g. genomic DNA, cDNA, mRNA, protein, or enzyme activity), or, alternatively, can be a qualitative assessment of the level of CYP24, in particular in comparison with a control level. The type of level being detected will be clear from the context. Because CYP24 activity is tightly linked to VDR activity, measurement of gene expression is preferably done in combination with a measurement of VDR activity.

To "compare" levels of CYP24 means to detect CYP24 levels in two samples and to determine whether the levels are equal or if one or the other is greater. A comparison can be done between quantified levels, allowing statistical comparison between the two values, or in the absence of quantification, for example using qualitative methods of detection such as visual assessment by a human.

A "control sample" refers to a sample of biological material representative of healthy, cancer-free animals, and/or cells or tissues. The level of CYP24 in a control sample is desirably typical of the general population of normal, cancer-free animals or of a particular individual at a particular time (e.g. before, during or after a treatment regimen), or in a particular tissue. This sample can be removed from an animal expressly for use in the methods described in this invention, or can be any biological material representative of normal, cancer-free animals, including cancer-free biological material taken from an animal with cancer elsewhere in its body. A control sample can also refer to an established level of CYP24, representative of the cancer-free population, that has been previously established based on measurements from normal, cancer-free animals.

An "increased level of CYP24" means a level of CYP24, that, in comparison with a control level of CYP24, is detectably higher. The method of comparison can be statistical, using quantified values for the level of CYP24, or can be compared using non-statistical means, such as by visual assessment by a human.

The "copy number of CYP24 genes" refers to the number of DNA sequences in a cell encoding a 25-hydroxyvitamin D3 24-hydroxylase enzyme. Generally, for a given gene, an animal has two copies of each gene. The copy number can be increased, however, by gene amplification or duplication, or reduced by deletion.

When a level of CYP24 mRNA, protein, enzyme activity, or copy number is "measured," it is assessed using qualitative or quantitative methods. Preferably, the level is determined using quantitative means, allowing the statistical comparison of values obtained from biological samples and control values. The level can also be determined using qualitative methods, such as the visual analysis and comparison by a human of multiple visibly labeled samples, e.g. fluorescently labeled samples detected using a fluorescent microscope or other optical detector (e.g. image analysis system, etc.). When a level of CYP24 mRNA, protein, or enzyme activity is measured the measurement preferably includes a measurement of VDR activity, and/or a measure of CYP24 activity in a normal tissue or cell (e.g. from the same animal or from a different "control" animal).

"25-hydroxyvitamin D3 24-hydroxylase enzyme activity" means the catalysis of the 24-hydroxylation of 25-hydroxyvitamin D3, 1,alpha-25 dihydroxyvitamin D3, or other analogous substrates (see, e.g., Stryer (1988) Biochemistry, $3^{rd}$ Ed., W.H. Freeman and Co.; Jehan et al., (1998) *Biochim Biophys Acta* 1395:259-265; Seo and Norman (1997) *J Bone Miner Res* 12:598-606).

"Tissue biopsy" refers to the removal of a biological sample for diagnostic analysis. In a patient with cancer, tissue may be removed from a tumor, allowing the analysis of cells within the tumor.

When a quantified level of CYP24 falls outside of a given confidence interval for a normal level of CYP24, the difference between the two levels is said to be "statistically significant." If a test value falls outside of a given confidence interval for a normal level of CYP24, it is possible to calculate the probability that the test value is truly abnormal and does not just represent a normal deviation from the average. In the methods of this invention, a difference between a test sample and a control can be termed "statistically significant" when the probability of the test sample being abnormal can be any of a number of values, including 0.15, 0.1, 0.05, and 0.01. Numerous sources teach how to assess statistical significance, such as Freund, J. E. (1988) Modern elementary statistics, Prentice-Hall.

The "survival expectancy" of an animal refers to a prognostic estimate of the outcome of a disease or condition. A "survival expectancy" can refer to a prediction regarding the severity, duration, or progress of a disease, condition, or any symptom thereof. "Survival expectancy" can also refer to the length of time an animal is expected to survive, or to the probability of the animal surviving until a certain time.

A "method of treating cancer" refers to a procedure or course of action that is designed to reduce or eliminate the number of cancer cells in an animal, or to alleviate the symptoms of a cancer. "A method of treating cancer" does not necessarily mean that the cancer cells will in fact be eliminated, that the number of cells will in fact be reduced, or that the symptoms of a cancer will in fact be alleviated. Often, a method of treating cancer will be performed even with a low likelihood of success, but which, given the medical history and estimated survival expectancy of an animal, is deemed an overall beneficial course of action.

"Reducing the level of CYP24 activity" refers to inhibiting the 25-hydroxyvitamin D3 24-hydroxylase enzyme activity in the cell, or lowering the copy number of CYP24 genes, or decreasing the level of CYP24 mRNA or protein in the cell (e.g., at a given VDR activity level). Preferably, the level of CYP24 activity is lowered to the level typical of a normal, cancer-free cell, but the level may be reduced to any level that is sufficient to decrease the proliferation of the cell, including to levels below those typical of normal cells.

"Contacting" a cell with vitamin D is to ensure that the cell is in the presence of vitamin D. In the case of a cell that is not naturally in contact with vitamin D, vitamin D is added to the cell, in vivo or in vitro. "Vitamin D" refers to any of the family of vitamin D molecules, including but not limited to vitamin D1, vitamin D2, and vitamin D3. It also refers to structural and functional homologs of these molecules, e.g. those that are substrates for the CYP24 enzyme, as well as metabolic products of vitamin D.

A "tumor cell" is a cancer cell that is part of a tumor, has been isolated from a tumor, or which is capable of forming a tumor. Tumor cells can exist in vivo or in vitro.

A "hyperproliferative cell" is a cell with an abnormally high rate of proliferation, or a cell that proliferates to an abnormally great extent, i.e. gives rise to a population of cells that increases in number over time. "Hyperproliferative cells" can exist in vitro or in vivo.

An "inhibitor of CYP24 activity" is a molecule that acts to reduce CYP24 activity, as defined above. Such inhibitors can include antisense molecules or ribozymes, repressors of CYP24 gene transcription, or competitive or non-competitive molecular inhibitors of the 25-hydroxyvitamin D3 24-hydroxylase enzyme.

The phrase "repressor of CYP24 transcription" refers to a molecule that can prevent the production of CYP24 mRNA from a CYP24 gene. Preferably, the molecule binds directly or indirectly to a regulatory element of the CYP24 gene, thereby preventing the transcription of the CYP24 gene.

A "competitive inhibitor of 25-hydroxyvitamin D3 24-hydroxylase" means a molecule that can bind directly or indirectly to a 25-hydroxyvitamin D3 24-hydroxylase enzyme or to its substrate, thereby preventing the binding of the enzyme to its substrate and preventing the 24-hydroxylation of the substrate, in vitro or in vivo.

The phrase "non-competitive inhibitor of 25-hydroxyvitamin D3 24-hydroxylase" refers to a molecule that prevents the 24-hydroxylation of a 25-hydroxyvitamin D3 24-hydroxylase enzyme substrate but which does not prevent the binding of the enzyme to the substrate.

"Screening" for an inhibitor of cell proliferation or of CYP24 activity means to systematically examine the ability of a population of molecules to inhibit cell proliferation or CYP24 activity. Screening can be done in vitro or in vivo. The inhibitory activity of the screened molecules can be assessed directly, e.g. by examining CYP24 enzyme activity using standard assays, or indirectly, e.g. by monitoring a cellular consequence of CYP24 enzyme activity, such as cell proliferation.

A "CYP24-expressing cell" is a cell that produces any amount of 25-hydroxyvitamin D3 24-hydroxylase protein. Generally, the amount of enzyme produced by the cell will be detectable using standard techniques.

A "test agent" is any molecule or non-molecular entity that is tested in a screen. The molecule may be randomly selected for inclusion in the screen, or may be included because of an a priori expectation that the molecule will give a positive result in the screen. The molecule may be directly introduced into a cell or a biochemical assay for the purposes of the screen, or it may comprise nucleic acids that encode a polypeptide or RNA that is desirably tested in the screen. Molecules introduced directly into an assay system can include any known chemical or biochemical molecule, including peptides, nucleic acids, carbohydrates, lipids, or any other organic or inorganic molecule. A "test agent" can also refer to non-molecular entities such as electromagnetic radiation or heat.

The "proliferation" of a cell refers to the rate at which the cell or population of cells grows and divides, or to the extent to which the cell or population of cells grows, divides, or increases in number. The "proliferation" of a cell can reflect multiple factors including the rate of cell growth and division and the rate of cell death.

The phrase "decreasing the proliferation of a cell" means to reduce the rate or extent of growth or division of a cell or population of cells. Such methods can involve preventing cell division or cell growth, and may also include cell killing, and can be practiced in vivo or in vitro.

"CYP24-inhibiting activity" is the ability of a molecule to reduce or prevent the production and/or accumulation of 25-hydroxyvitamin D3 24-hydroxylase enzyme activity in a cell. The molecule can prevent the accumulation at any step of the pathway from the CYP24 gene to enzyme activity, e.g. preventing transcription, reducing mRNA levels, preventing translation, or inhibiting the enzyme itself. The reduction or prevention is preferably ascertained by reference to a control at the same level of VDR activity.

A CYP24 enzyme or CYP24 polypeptide is a protein with 25-hydroxyvitamin D3 24-hydroxylase activity and is most preferably encoded by a CYP24 gene.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

An amino acid, identified by name herein "e.g., arginine" or "arginine residue" as used herein refers to natural, synthetic, or version of the amino acids Thus, for example, an arginine can also include arginine analogs that offer the same or similar functionality as natural arginine with respect to their ability to be incorporated into a polypeptide, effect folding of that polypeptide and effect interactions of that polypeptide with other polypeptide(s).

DETAILED DESCRIPTION

Figure 1:
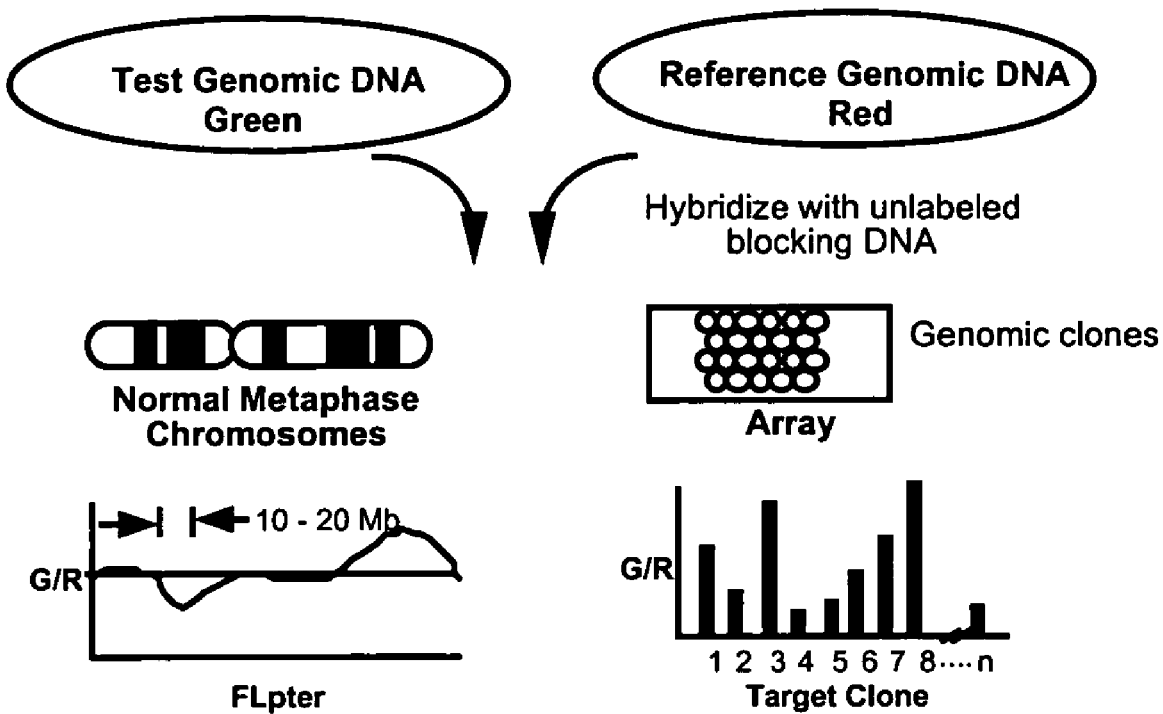
FIG. 1 illustrates Comparative Genomic Hybridization (CGH). In the left panel, total genomic DNAs are isolated from a "test" and a "reference" cell population, labeled with different fluorochromes, and hybridized to normal metaphase chromosomes. Cot-1 DNA is used to suppress hybridization of repetitive sequences. The resulting ratio of the fluorescence intensities of the two fluorochromes at a location on a chromosome is approximately proportional to the ratio of the copy numbers of the corresponding DNA sequences in the test and reference genomes. The right panel shows a similar hybridization to an array of mapped clones. This permits measurement of copy number with resolution determined by the size of the clones and/or the map spacing between them.
Figure 2:
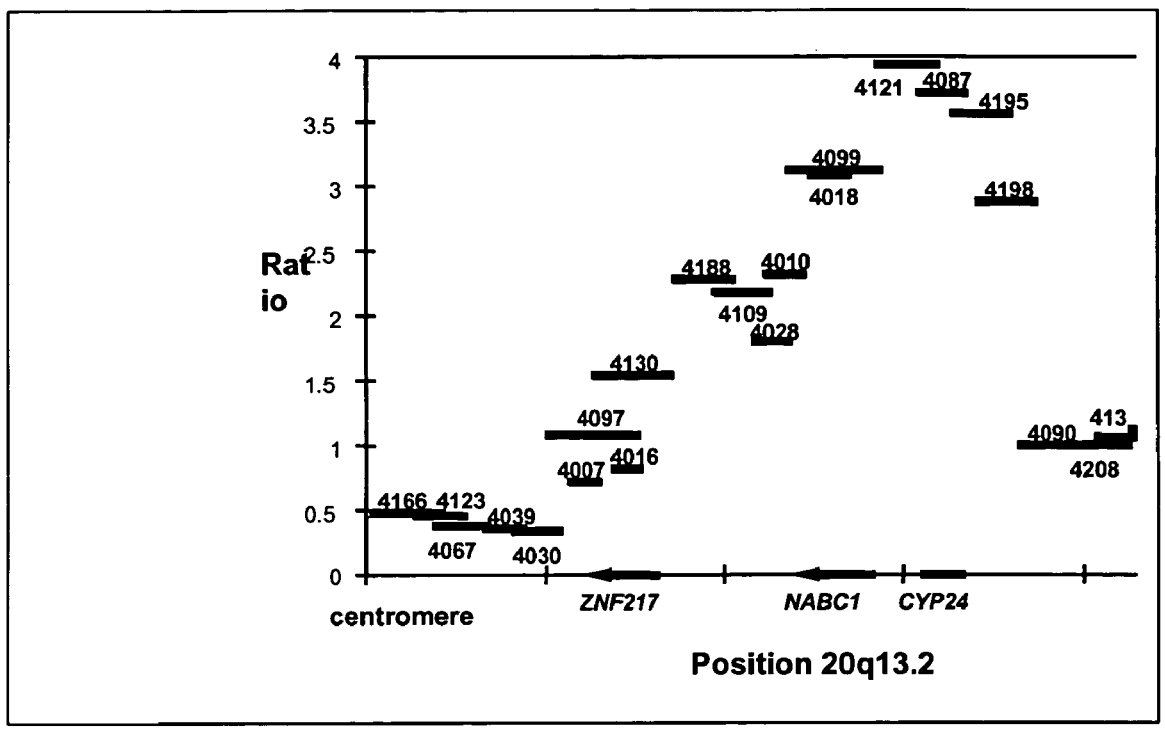
FIG. 2 illustrates a high resolution array CGH measurement on the breast cancer tumor, S21. The test:reference ratios for contiguous target clones from region A at 20q13.2 are plotted with the ratio on each target clone shown as a bar, representing the clone overlaps as determined by STS-content mapping. Clone names have been shortened to the last four digits. The analysis indicates that the overlapping clones, RMC20B4121, RMC20B4087, and RMC20B4195 are the locus of the peak in the copy number profile and that copy number in the region decreases precipitously distal to the overlapping clones, RMC20B4087 and RMC20B4195.

This invention pertains to the discovery that that amplification of the vitamin D 24 hydroxylase (CYP24) gene (GenBank Accession Numbers U60669 S78775 and X59506) occurs in various cancers (e.g., breast tumors). Vitamin D 24 hydroxylase controls activity of the vitamin D system in cells by initiating degradation of the active form of vitamin D3. Without being bound by a particular theory, it is believed that amplification of CYP24 during tumor evolution provides a means to disrupt vitamin D mediated growth control.

Amplification of chromosome band 20q13.2 in human breast cancer is associated with poor prognosis and aggressive tumor behavior (Tanner et al., (1995) *Clin. Cancer Res.* 1: 1455-1461; Courjal et al. (1996) *Br. J. Cancer,* 74: 1984-1989), suggesting that overexpression of genes mapping to this region is likely to contribute to the development of breast cancer. Using a new high resolution form of comparative genomic hybridization, array CGH (Pinkel et al. (1998) *Nature Genetics,* 20: 207-211), we mapped DNA copy number profiles across the region of recurrent amplification at 20q13.2.

This analysis focused attention on the gene CYP24, because it mapped to the narrow genomic interval that is most highly amplified in the most informative tumors and because of existing knowledge of CYP24 function. CYP24 encodes vitamin D 24 hydroxylase, an enzyme that catalyzes degradation of the active form of vitamin D, 1,25-dihydroxy-D3 (for reviews, see Walters (1992) *Endocrine Reviews* 13: 719-764; Jones et al. (1998) *Amer. Physiol. Soc.* 78: 1193-1231). Vitamin D is a secosteroid hormone that plays a major role in the regulation of calcium and bone metabolism. However, vitamin D receptors (VDR) have also been found in many other so-called "non-classical" tissues not involved in mineral metabolism, including the breast (Berger et al. (1987) *Cancer Res.* 47: 6793-6799; Buras et al. (1994) *Breast Cancer Res. and Treatment* 31: 191-202), indicating a role for vitamin D in these tissues also. Levels of 1,25-dihydroxy-D3 and ligand bound receptor appear to be very tightly controlled in cells by a feedback mechanism. Binding of the hormone to the VDR results in activation of CYP24 transcription to initiate degradation of 1,25-dihydroxy-D3 and inhibition of CYP1, the enzyme required for synthesis of 1,25-dihydroxy-D3. In fact, transcription of CYP24 is so closely coupled to VDR levels and activity that activation of transcription from a CYP24 promoter-reporter construct is used as an assay for VDR activity (Arbour et al. (1998) *Anal. Biochem.* 255: 148-154). Thus, without being bound to this theory, we believe the role of CYP24 in cells is to limit the biological activity of the vitamin D system.

In the "non-classical" tissues such as breast, vitamin D promotes growth inhibition by directing cells towards differentiation and cessation of proliferation. Breast cancer cells respond to the antiproliferative effects of vitamin D both in vivo and in vitro (Eisman et al. (1989) *Cancer Res.* 47: 21-25). Breast cancer cell lines generally arrest in the G0/G1 stage of the cell cycle in response to vitamin D, and the MCF-7 breast cancer cell line can be induced to enter apoptosis (Elstner et al. (1995) *Cancer Res.* 55: 2822-2830; Love-Schimenti et al. (1996) *Cancer Res.* 56: 2789-2794; Simboli-Campbell et al. (1997) *Breast Cancer Res. and Treatment*, 42: 31-41). Administration of vitamin D to rodents reduces progression of tumor xenografts (Eisman et al. (1989) *Cancer Res.* 47: 21-25; Colston et al. (1989) *Lancet*, 188-191).

These growth modulatory properties of vitamin D support the present belief that disruption of the vitamin D system is likely to contribute to neoplasia. This suggestion is further supported by the observation that patients with receptor negative tumors have a poorer prognosis and by epidemiological studies that have established that exposure to sunlight and risk of breast and colon cancer (Gorham et al. (1989) *Can. J. Public Health* 80: 96-100; Gorham et al. (1990) *Int. J. Epidemiol.* 19: 820-824; Garland et al. (1990) *Preventive Medicine* 19: 614-622) are inversely correlated.

Thus, the present hypothesized oncogenic role of CYP24 derives from its function to reduce levels of 1,25-dihydroxyvitamin-D3 and so modulate the biological effects of ligand bound VDR. This hypothesis is supported by the observation that the antiproliferative activity of vitamin D in vitro is enhanced in the presence of hydroxylase inhibitors (Reinhardt and Horst (1989) *Arch. Biochem. Biophys.* 272: 459-465; Zhao et al. (1996) *J. Steroid. Biochem. Mol. Biol.* 57: 197-202). Thus, without being bound by a theory, the present invention is predicated, in part, on the recognition that amplification of CYP24 abrogates vitamin D mediated growth control by up-regulation of vitamin D degradation in cells, since ligand bound VDR will bind to and initiate transcription from an increased number of CYP24 gene copies.

In view of these discoveries, CYP24 provides a good marker for a cancer and/or for the likelihood of (predilection to) development of a cancer. Thus, in one embodiment, this invention provides methods of detecting the presence of, or a predisposition to, cancer in an animal. The methods involve (i) providing a biological sample from an animal (e.g. a human patient); (ii) detecting the level of CYP24 within the biological sample; and (iii) comparing the level of CYP24 with a level of CYP24 in a control sample taken from a normal, cancer-free animal where an increased level of CYP24 in the biological sample compared to the level of CYP24 in the control sample indicates the presence of said cancer in said animal. Where the CYP24 transcript, translated polypeptide, or enzymatic activity is assayed, the methods preferably include a measurement of VDR activity and the comparison between sample and control is made at the same VDR level or corrections are made reflecting differences in VDR level.

Similarly, the detection of CYP24 level can also be used to estimate the survival expectancy of an animal with cancer. Because CYP24 level can be used to assay survival expectancy (e.g. likelihood of progression or recurrence of the disease), an assay of CYP24 level provides a useful component of a cancer therapy. Thus, in one preferred method of treating cancer, CYP24 level is assayed and, where it is high relative to the appropriate control or population standard, one or more adjuvant therapies (e.g. radiation therapy, resurgery, chemotherapy, etc.) are selected for the cancer treatment regimen.

Having identified elevated CYP24 levels as indicative of a cancer or a predisposition to cancer, CYP24 level provides a useful target/marker for evaluating potential prophylaxis and/ or therapeutics. Thus, for example, the level of CYP24 activity (at a given level of VDR activity) in the presence or absence of one or more putative potential therapeutics or prophylactics provides a measure of the potential activity of the therapeutic/prophylactic compound, i.e., a lower CYP24 activity in the presence of the compound indicates higher potential activity of the compound.

In another embodiment this invention provides a method of decreasing the proliferation of a cell (e.g. a cancer cell). The method involves reducing the level of CYP24 activity in said cell using an inhibitor of CYP24.

I. Assays of CYP24 Level.

As indicated above, assays of CYP24 copy number or level of activity (e.g., at a particular vitamin D receptor activity) provide a measure of the presence or likelihood of (predisposition to) a cancer. The sequence of CYP24 is known and hence, copy number can be directly measured according to a number of different methods as described below.

With respect to assays based on CYP24 "activity" level (e.g., level of transcript, level of translated protein, level of protein enzymatic activity), the close coupling of transcription of CYP24 to vitamin D receptor (VDR) level and activity complicates the evaluation of CYP24 level. In short, CYP24 expression levels depend on VDR activity as well as the magnitude of transcription resulting from copy number increases. Thus, particularly in embodiments relying on assays of CYP24 "activity", evaluation of CYP24 levels preferably involves measurement not only of CYP24 levels in tumor cells relative to normal tissue, but also the VDR levels and activities in the tumors and normal tissues. Such assays are described below.

A) Detection of Copy Number

In one embodiment, the presence of, or predilection to cancer, is evaluated simply by a determination of CYP24 copy number. Methods of evaluating the copy number of a particular gene are well known to those of skill in the art.

1) Hybridization-Based Assays

One method for evaluating the copy number of CYP24-encoding nucleic acid in a sample involves a Southern transfer. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid.

An alternative means for determining the copy number of CYP24 is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate-(e.g. membrane or glass) bound methods or array-based approaches as described below.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bp to about 1000 bases.

In some applications it is necessary to block the hybridization capacity of repetitive sequences. Thus, in some embodiments, tRNA, human genomic DNA, or Cot-1 DNA is used to block non-specific hybridization.

In comparative genomic hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the CYP24 copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol.* 33: *In Situ Hybridization Protocols*, Choo, ed., Humana Press, Totowa, N.J. (1994), etc. In one particularly preferred embodiment, the hybridization protocol of Pinkel et al. (1998) *Nature Genetics* 20: 207-211, or of Kallioniemi (1992) *Proc. Natl Acad Sci USA* 89:5321-5325 (1992) is used.

2) Amplification-Based Assays.

In still another embodiment, amplification-based assays can be used to measure copy number. In such amplification-based assays, the CYP24 nucleic acid sequences act as a template in an amplification reaction (e.g. Polymerase Chain Reaction (PCR). In a quantitative amplification, the amount of amplification product will be proportional to the amount of template in the original sample. Comparison to appropriate (e.g. healthy tissue) controls provides a measure of the copy number of CYP24.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). The known nucleic acid sequence for CYP24 (see, GenBank Accession Numbers U60669 S78775 and X59506) is sufficient to enable one of skill to routinely select primers to amplify any portion of the gene.

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

B) Detection of Gene Expression

As indicated above, CYP24 level can also be assayed as a marker for a predilection to cancer. However, because of the close coupling of transcription of CYP24 to vitamin D receptor (VDR) level measures of CYP24 "activity" are preferably coupled with measures of VDR activity for use in the assays of this invention. Thus, an elevation of CYP24 activity, compared to a control at the same level of VDR activity, provides an indication of the presence and/or predilection to a cancer.

In preferred embodiments, CYP24 activity is characterized by a measure of CYP24 gene transcript (e.g. mRNA), by a measure of the quantity of translated protein, or by a measure of CYP24 enzymatic activity (25-hydroxyvitamin D3 24-hydroxylase enzyme activity).

1) Detection of Gene Transcript.

a) Direct Hybridization Based Assays.

Methods of detecting and/or quantifying the CYP24 gene transcript (CYP24 mRNA or cDNA made therefrom) using nucleic acid hybridization techniques are known to those of skill in the art (see Sambrook et al. supra). For example, one method for evaluating the presence, absence, or quantity of CYP24 cDNA involves a Southern transfer as described above. Briefly, the CYP24 mRNA is isolated (e.g. using an acid guanidinium-phenol-chloroform extraction method, Sambrook et al. supra.) and reverse transcribed to produce cDNA. The cDNA is then optionally digested and run on a gels in buffer and transferred to membranes. Hybridization is then carried out using the nucleic acid probes specific for the target CYP24 cDNA.

The probes can be full length or less than the full length of the nucleic acid sequence encoding the CYP24 protein. Shorter probes are empirically tested for specificity. Preferably nucleic acid probes are 20 bases or longer in length. (See Sambrook et al. for methods of selecting nucleic acid probe sequences for use in nucleic acid hybridization.) Visualization of the hybridized portions allows the qualitative determination of the presence or absence of CYP24 cDNA.

Similarly, a Northern transfer may be used for the detection of CYP24 mRNA directly. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the CYP24 mRNA.

b) Amplification-Based Assays.

In another preferred embodiment, CYP24 transcript (e.g., CYP24 mRNA) can be measured using amplification (e.g. PCR) based methods as described above for directly assessing copy number of CYP24 DNA. In a preferred embodiment, CYP24 transcript level is assessed by using reverse transcription PCR (RT-PCR). As mentioned above, because CYP24 activity is tightly linked to vitamin D receptor (VDR) activity, where gene transcript level is being measured it is preferable to also measure VDR activity (e.g. transcript level). Then, an increase in CYP24 activity for a given level of VDR activity indicates a cancer or an increased predisposition to cancer. Thus, in preferred amplification-based assays (e.g. RT-PCR) the level of VDR transcript is also assayed.

As indicated above, PCR assay methods are well known to those of skill in the art. Similarly, RT-PCR methods are also well known. Moreover, probes for such an RT-PCR assay are provided below in Table 1 and the assay is illustrated in Example 1 (see, e.g., FIG. 3).

2) Detection of Expressed Protein

The "activity" of CYP24 can also be detected and/or quantified by detecting or quantifying the expressed CYP24 polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the CYP24 polypeptide is detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

In another preferred embodiment, Western blot (immuno-blot) analysis is used to detect and quantify the presence of CYP24 polypeptide in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind CYP24 polypeptide. The anti-CYP24 polypeptide antibodies specifically bind to CYP24 on the solid support. These antibodies may be directly labeled or alternatively may be subsequently detected using labeled antibodies (e.g., labeled sheep anti-mouse antibodies) that specifically bind to the anti-CYP24.

In a more preferred embodiment, the CYP24 polypeptide is detected using an immunoassay. As used herein, an immunoassay is an assay that utilizes an antibody to specifically bind to the analyte (CYP24 polypeptide). The immunoassay is thus characterized by detection of specific binding of a CYP24 polypeptide to an anti-CYP24 antibody as opposed to the use of other physical or chemical properties to isolate, target, and quantify the analyte.

The CYP24 polypeptide is detected and/or quantified using any of a number of well recognized immunological binding assays (see, e.g., U.S. Pat. Nos. 4,366,241; 4,376,110; 4,517, 288; and 4,837,168). For a review of the general immunoassays, see also Asai (1993) *Methods in Cell Biology Volume 37: Antibodies in Cell Biology*, Academic Press, Inc. New York; Stites & Terr (1991) *Basic and Clinical Immunology 7th Edition*.

Immunological binding assays (or immunoassays) typically utilize a "capture agent" to specifically bind to and often immobilize the analyte (in this case CYP24 polypeptide or subsequence). The capture agent is a moiety that specifically binds to the analyte. In a preferred embodiment, the capture agent is an antibody that specifically binds a CYP24 polypeptide. The antibody (anti-CYP24) may be produced by any of a number of means well known to those of skill in the art.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled CYP24 polypeptide or a labeled anti-CYP24 antibody. Alternatively, the labeling agent may be a third moiety, such as another antibody, that specifically binds to the antibody/CYP24 polypeptide complex.

In one preferred embodiment, the labeling agent is a second human CYP24 antibody bearing a label. Alternatively, the second CYP24 antibody may lack a label, but it may, in turn, be bound by a labeled third antibody specific to antibodies of the species from which the second antibody is derived. The second can be modified with a detectable moiety, e.g., as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

As indicated above, immunoassays for the detection and/or quantification of CYP24 polypeptide can take a wide variety of formats well known to those of skill in the art.

Preferred immunoassays for detecting CYP24 polypeptide are either competitive or noncompetitive. Noncompetitive immunoassays are assays in which the amount of captured analyte is directly measured. In one preferred "sandwich" assay, for example, the capture agent (anti-CYP24 antibodies) can be bound directly to a solid substrate where they are immobilized. These immobilized antibodies then capture CYP24 polypeptide present in the test sample. The CYP24 thus immobilized is then bound by a labeling agent, such as a second human CYP24 antibody bearing a label.

In competitive assays, the amount of analyte (CYP24 polypeptide) present in the sample is measured indirectly by measuring the amount of an added (exogenous) analyte (CYP24 polypeptide) displaced (or competed away) from a capture agent (anti CYP24 antibody) by the analyte present in the sample. In one competitive assay, a known amount of, in this case, CYP24 polypeptide is added to the sample and the sample is then contacted with a capture agent. The amount of CYP24 polypeptide bound to the antibody is inversely proportional to the concentration of CYP24 polypeptide present in the sample.

In one particularly preferred embodiment, the antibody is immobilized on a solid substrate. The amount of CYP24 polypeptide bound to the antibody may be determined either by measuring the amount of CYP24 polypeptide present in an CYP24 polypeptide/antibody complex, or alternatively by measuring the amount of remaining uncomplexed CYP24 polypeptide. The amount of CYP24 polypeptide may be detected by providing a labeled CYP24 polypeptide.

The assays of this invention are scored (as positive or negative or quantity of CYP24 polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of CYP24.

Antibodies for use in the various immunoassays described herein, can be produced as described below.

3) Detection of Enzyme Activity.

In another embodiment, CYP24 level (activity) is assayed by measuring the enzymatic activity of the CYP24 polypeptide (25-hydroxyvitamin D3 24-hydroxylase enzyme). Methods of assaying the activity of this enzyme are well known to those of skill in the art. Thus, for example, CYP24 activity in cell suspensions will be assayed by measuring the metabolism of $^3$H-labeled 25OHD3 (Amersham). The oxidation products are separated by HPLC and the activity calculated as the sum of the C-24 oxidation products (Tomon et al., 1990 *Endocrinol.*, 126: 2868-2875). Alternatively, the CYP24 activity can be determined after incubation with 25-OH-[26, 27-$^3$H]D$_3$ (NEN #NET349) and measurement of radioactivity released as [$^3$H]acetone after periodate cleavage (Beckman and DeLuca (1997) *Meth. Enzymol.*, 282: 200-213).

C) Comparison of CYP24 Levels while Controlling for VDR Activity.

As explained above, the activity level of CYP24 is tightly linked to the activity level of the vitamin D receptor (VDR). Thus, when assaying CYP24 activity (e.g. transcription, translation, activity of translated protein, etc.) the activity level is preferably determined with respect to the VDR activity level. When a sample tissue (e.g. tissue biopsy) shows a higher level of CYP24 activity than a control sample (e.g. healthy tissue) (preferably at the same level of VDR activity) then the elevated CYP24 activity indicates the presence of, prognosis of, or predisposition to develop, a cancer.

The VDR transcript (e.g., mRNA) levels or translated protein levels can be measured using the assays described above for CYP24 activity; the only difference being that the assay is adjusted for specificity to VDR nucleic acids or polypeptides rather than to CYP24.

Antibodies specific for VDR are commercially available (Affinity BioReagents #PA1-711, MA1-710, Santa Cruz Biotechnology # sc-1008, sc-1009). Gene specific probes for CYP24 and VDR mRNAs that can be used to generate riboprobes for mRNA FISH are provided in Example 1. In addition, an assay for CYP24 and VDR transcription levels is illustrated in Example 1.

D) Hybridization Formats and Optimization of Hybridization Conditions.

1) Array-Based Hybridization Formats.

The methods of this invention are particularly well suited to array-based hybridization formats. For a description of one preferred array-based hybridization system see Pinkel et al. (1998) *Nature Genetics,* 20: 207-211.

Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays.

In brief, the light-directed combinatorial synthesis of oligonucleotide arrays on glass surfaces proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In a preferred embodiment, the arrays used in this invention can comprise either probe or target nucleic acids. These probes or target nucleic acids are then hybridized respectively with their "target" nucleic acids. Because the CYP24 gene sequence is known, oligonucleotide arrays can be synthesized containing one or multiple probes specific to CYP24.

In another embodiment the array, particularly a spotted array, can include genomic DNA, e.g. overlapping clones that provide a high resolution scan of the amplicon containing to CYP24, or of CYP24 itself. Amplicon nucleic acid can be obtained from, e.g., HACs, MACs, YACs, BACs, PACs, P1s, cosmids, plasmids, inter-Alu PCR products of genomic clones, restriction digests of genomic clones, cDNA clones, amplification (e.g., PCR) products, and the like.

In various embodiments, the array nucleic acids are derived from previously mapped libraries of clones spanning or including the amplicon sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.*, 164: 336-344; Kremsky (1987) *Nucl. Acids Res.* 15: 2891-2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 µm can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup (1994) *Cytometry* 16:206-213, Pinkel et al. (1998) *Nature Genetics* 20: 207-211).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122-1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, probe nucleic acid is spotted onto a surface (e.g., a glass or quartz surface). The nucleic acid is dissolved in a mixture of water, dimethylsulfoxide (DMSO), and nitrocellulose and spotted onto amino-silane coated glass slides. Small capillaries tubes can be used to "spot" the probe mixture.

2) Other Hybridization Formats.

A variety of nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides.

The most common method of detection is the use of autoradiography with $^3H$, $^{125}I$, $^{35}S$, $^{14}C$, or $^{32}P$-labelled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

3) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., tRNA, sperm DNA, cot-1 DNA, etc.) during the hybridization to reduce non-specific binding. In a particularly preferred embodiment, the hybridization is performed in the presence of about 10 μg/1 μL tRNA. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

4) Labeling and Detection of Nucleic Acids.

In a preferred embodiment, the hybridized nucleic acids are detected by detecting one or more labels attached to the sample nucleic acids. The labels may be incorporated by any of a number of means well known to those of skill in the art. Means of attaching labels to nucleic acids include, for example nick translation, or end-labeling by kinasing of the nucleic acid and subsequent attachment (ligation) of a linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends.

As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily aderivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016-2018).

E) Antibodies to CYP24.

Either polyclonal or monoclonal antibodies may be used in the immunoassays and therapeutic methods of the invention described herein. Polyclonal antibodies are preferably raised by multiple injections (e.g. subcutaneous or intramuscular injections) of substantially pure CYP24 polypeptides or antigenic CYP24 polypeptides into a suitable non-human mammal. The antigenicity of CYP24 peptides can be determined by conventional techniques to determine the magnitude of the antibody response of an animal that has been immunized with the peptide. Generally, the CYP24 peptides that are used to raise the anti-CYP24 antibodies should generally be those which induce production of high titers of antibody with relatively high affinity for CYP24.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because CYP24 may be conserved among mammalian species, use of a carrier protein to enhance the immunogenicity of CYP24 proteins is preferred.

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the CYP24 antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')^{2'}$ which are capable of binding an epitopic determinant. Also, in this context, the term "mab's of the invention" refers to monoclonal antibodies with specificity for CYP24.

The general method used for production of hybridomas secreting mAbs is well known (Kohler and Milstein (1975) *Nature,* 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines.

Confirmation of CYP24 specificity among mAb's can be accomplished using relatively routine screening techniques (such as the enzyme-linked immunosorbent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to CYP24 isolated as described above. If the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to preincubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment from a library of greater than $10^{10}$ nonbinding clones. To express antibody fragments on the surface of phage (phage display), an antibody fragment gene is inserted into the gene encoding a phage surface protein (pIII) and the antibody fragment-pIII fusion protein is displayed on the phage surface (McCafferty et al. (1990) *Nature,* 348: 552-554; Hoogenboom et al. (1991) *Nucleic Acids Res.* 19: 4133-4137).

Since the antibody fragments on the surface of the phage are functional, phage bearing antigen binding antibody fragments can be separated from non-binding phage by antigen affinity chromatography (McCafferty et al. (1990) *Nature,* 348: 552-554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature,* 348: 552-554). Thus even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581-597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581-597; Marks et al. (1993). *Bio/Technology.* 10: 779-783; Griffiths et al. (1993) *EMBO J.* 12: 725-734; Clackson et al. (1991) *Nature.* 352: 624-628). Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

It will also be recognized that CYP24 antibodies can be prepared by any of a number of commercial services (e.g., Berkeley antibody laboratories, Bethyl Laboratories, Anawa, Eurogenetec, etc.).

II. Assay Optimization—Determining Prognostically Significant Levels.

The assays of this invention have immediate utility in detecting/predicting the likelihood of a cancer, in estimating survival from a cancer, in screening for agents that modulate CYP24 activity, and in screening for agents that inhibit cell proliferation. In particular, for example, identification of an amplification in CYP24 (genomic DNA) indicates the presence of a cancer and/or the predisposition to develop a cancer.

Methods of optimizing predictive/diagnostic assays are well known to those of ordinary skill in the art. Typically this involves determining "baseline levels" (e.g. of CYP24) in normal tissues and CYP24 activity levels in pathological (i.e. tumor tissues). In particularly preferred embodiments, such levels are determined with appropriate controls for concurrent VDR activity, sample type, age, sex, developmental state, overall physiological state (e.g. in a non-pregnant as compared to a pregnant female), overall health, tumor type, etc. In a preferred embodiment, "baseline" (e.g., control) levels are determined from a normal (healthy) tissue from the same individual or from individuals of the same population. Alternatively, "baseline" and "pathological" levels are determined from "population" studies" that provide sufficient sample size and diversity that the influence of the various co-factors identified above (age, health, sex, etc.) can be of statistically evaluated. "Baseline" CYP24 levels can also be evaluated by reference to model systems, e.g., as described in Examples 3-5.

In a preferred embodiment, quantitative assays of CYP24 level are deemed to show a positive result, e.g. elevated CYP24 level, when the measured CYP24 level is greater than the level measured or known for a control sample (e.g. either a level known or measured for a normal healthy mammal of the same species or a "baseline/reference" level determined at a different tissue and/or a different time for the same individual. In a particularly preferred embodiment, the assay is deemed to show a positive result (e.g., "a prognostically significant level") when the difference between sample and "control" is statistically significant (e.g. at the 85% or greater, preferably at the 90% or greater, more preferably at the 95% or greater and most preferably at the 98% or greater confidence level).

III. Methods of Treating Cancer—Selection of Adjuvant Therapy Based on CYP24 Level.

Because of the ability to evaluate the presence of, or the predisposition to develop, a cancer, the assays of this invention make a useful component of a cancer therapy regimen. Thus, in one embodiment, CYP24 activity can be used as a measure of disease progression, while in another embodiment CYP24 activity is used to evaluate the necessity of an adjuvant therapy.

"Adjuvant cancer therapy" refers to a method of treating cancer, such as chemotherapy, radiation therapy, surgery, reoperation, antihormone therapy, and immunotherapy, that is administered in combination with or following another method of cancer treatment. An "adjuvant cancer therapy" often represents an aggressive form of cancer treatment that is selected in view of a reduced survival expectancy and/or a detected level of CYP24 that is elevated compared to a control level.

Adjuvant therapies are well known to those of skill in the art and include, but are not limited to chemotherapy, radiation therapy, primary surgery or reoperation, antihormone therapy, immunotherapy, and the like. "Chemotherapy", as used in this context, refers to the administration of chemical compounds to an animal with cancer that is aimed at killing or reducing the number of cancer cells within the animal. Generally, chemotherapeutic agents arrest the growth of or kill cells that are dividing or growing, such as cancer cells. Chemotherapeutic agents for use against cancer are well known to those of skill in the art include, but are not limited to doxirubicin, vinblastine, genistein, etc.

"Radiation therapy" in this context refers to the administration of radioactivity to an animal with cancer. Radiation kills or inhibits the growth of dividing cells, such as cancer cells. The administration may be by an external source (e.g., a gamma source, a proton source, a molecular beam source, etc.) or may be by an implantable radioactive material. Radiation therapy includes "traditional" radiation treatment aimed at reduction or elimination of tumor volume or more aggressive radio-surgery techniques.

Surgical methods refer to the direct removal or ablation of cells, e.g. cancer cells, from an animal. Most often, the cancer cells will be in the form of a tumor (e.g. a mammary tumor), which is removed from the animal. The surgical methods may involve removal of healthy as well as pathological tissue. "Reoperation" refers to surgery performed on an animal that has previously undergone surgery for treatment of the same pathology.

"Antihormone therapy" refers to the administration of compounds that counteract or inhibit hormones, such as estrogen or androgen, that have a mitogenic effect on cells. Often, these hormones act to increase the cancerous properties of cancer cells in vivo.

Immunotherapy refers to methods of enhancing the ability of an animal's immune system to destroy cancer cells within the animal. This can involve the treatment with polyclonal or monoclonal antibodies that bind particular tumor-specific markers (e.g. IL-13 receptor, and Lewis Y ($Le^Y$) marker, etc.) help to direct cytotoxins of native immune system effectors to the tumor target. Immunotherapeutic methods are well know to those of skill in the art (see, e.g, Pastan et al. (1992) *Ann. Rev. Biochem.*, 61: 331-354, Brinkman and Pastan (1994) *Biochimica Biphysica Acta*, 1198: 27-45, etc.).

IV. Screening for Therapeutics

It was also a discovery of this invention that downregulation of CYP24 activity (at a given level of vitamin D receptor activity) is expected to act prophylactically to prevent the development of cancers and/or to act therapeutically to reduce or eliminate a cancer. Thus, in one embodiment, this invention provides methods of screening for agents that modulate and preferably that down regulate CYP24 activity. Downregulation, as used in this context, includes decrease in CYP24 transcription and/or decrease in CYP24 translation, and/or decrease in CYP24 polypeptide activity.

Preferred "screening" methods of this invention involve contacting a CYP24-expressing cell (e.g., a cell capable of expressing CYP24) with a test agent; and (ii) detecting the level of CYP24 activity (e.g. as described above), where a decreased level of CYP24 activity as compared to the level of CYP24 activity in a cell not contacted with the agent indicates that said agent inhibits or downregulates CYP24 and/or inhibits proliferation of the cell.

Virtually any agent can be tested in such an assay. Such agents include, but are not limited to natural or synthetic nucleic acids, natural or synthetic polypeptides, natural or synthetic lipids, natural or synthetic small organic molecules, and the like. In one preferred format, test agents are provided as members of a combinatorial library.

A) Combinatorial Libraries (e.g., Small Organic Molecules).

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described below to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909-6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217-9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) Nature Biotechnology, 14(3): 309-314), and PCT/US96/10287), carbohydrate libraries (see, e.g., Liang et al. (1996) Science, 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Screening

Any of the assays for compounds modulating CYP24 level described herein are amenable to high throughput screening. Preferred assays thus detect enhancement or inhibition of CYP24 gene transcription, inhibition or enhancement of CYP24 polypeptide expression, and inhibition or enhancement of CYP24 polypeptide activity, (at a given VDR activity level).

High throughput assays for the presence, absence, or quantification of particular nucleic acids or protein products are well known to those of skill in the art. Similarly, binding assays and reporter gene assays are similarly well known.

Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

V. Reducing CYP24 Activity Levels in Cells

In another embodiment, this invention provides methods of reducing CYP24 activity levels in a cell. In this context, a reduction of CYP24 activity is a decrease in CYP24 activity as compared to the same cell in an "untreated" condition. More preferably as compared to the same cell at the same level of VDR activity or normalized for VDR activity.

Methods of reducing activity levels of a particular gene or gene product are well known to those of skill in the art. Such methods include, but are not limited to targeting transcription or translation, e.g. by the use of antisense molecules or ribozymes, by targeting transcription factors, e.g. with antibodies or DNA binding proteins, and by targeting the polypeptide product, e.g. by competition with inactive binding agents (e.g. muteins), by direct blocking, e.g. by binding with antibodies or other ligands, etc.

A) Antisense Molecules.

CYP24 activity can be downregulated, or entirely inhibited, by the use of antisense molecules. An "antisense sequence or antisense nucleic acid" is a nucleic acid is complementary to the coding CYP24 mRNA nucleic acid sequence or a subsequence thereof. Binding of the antisense molecule to the CYP24 mRNA interferes with normal translation of the CYP24 polypeptide.

Thus, in accordance with preferred embodiments of this invention, preferred antisense molecules include nucleic acids (e.g. oligonucleotides and oligonucleotide analogs) that are hybridizable with CYP24 messenger RNA. This relationship is commonly denominated as "antisense." The antisense nucleic acids analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of CYP24 polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species which are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Oligonucleotides may also include species that include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of CYP24 to inhibit the function of that RNA.

The oligonucleotides in accordance with this invention preferably comprise from about 3 to about 100 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. The preparation of other oligonucleotides such as phosphorothioates and alkylated derivatives is also well known to those of skill in the art.

B) Ribozymes

In addition to antisense molecules, ribozymes can be used to target and inhibit transcription of CYP24. A ribozyme is an RNA molecule that catalytically cleaves other RNA molecules. Different kinds of ribozymes have been described, including group I ribozymes, hammerhead ribozymes, hairpin ribozymes, RNAse P, and axhead ribozymes (see Castanotto et al. (1994) *Adv. in Pharmacology* 25: 289-317 for a general review of the properties of different ribozymes).

The general features of hairpin ribozymes are described e.g., in Hampel et al. (1990) *Nucl. Acids Res.* 18: 299-304; Hampel et al. (1990) European Patent Publication No. 0 360 257; U.S. Pat. No. 5,254,678. Methods of preparing are well known to those of skill in the art (see, e.g., Wong-Staal et al., WO 94/26877; Ojwang et al. (1993) *Proc. Natl. Acad. Sci. USA* 90: 6340-6344; Yamada et al. (1994) *Human Gene Therapy* 1: 39-45; Leavitt et al. (1995) *Proc. Natl. Acad. Sci. USA* 92: 699-703; Leavitt et al. (1994) *Human Gene Therapy* 5: 1151-120; and Yamada et al. (1994) *Virology* 205: 121-126).

C) Competitive Inhibition of CYP24 Polypeptide Activity.

CYP24 activity, e.g., at a given VDR activity level, can be decreased by provision of a competitive inhibitor of the CYP24 polypeptide. This is most simply accomplished by providing a CYP24 polypeptide that lacks 25-hydroxyvitamin D3 24-hydroxylase enzyme activity.

Methods of making inactive polypeptide variants (muteins) are well known to those of skill (see, e.g., U.S. Pat. Nos. 5,486,463, 5,422,260, 5,116,943, 4,752,585, 4,518,504). Screening of such polypeptides (e.g., in the assays described above) can be accomplished with only routine experimentation. Using high-throughput methods, as described herein, literally thousands of agents can be screened in only a day or two.

D) Modification of Promoters to Regulate Endogenous CYP24 Expression.

In still another embodiment, the expression of CYP24 can be altered by altering the endogenous promoter. Methods of altering expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of the CYP24 gene is altered.

This is typically accomplished by the use of homologous recombination to introduce a heterologous nucleic acid into the native regulatory sequences. To down-regulate expression of the CYP24 gene product, simple mutations that either alter the reading frame or disrupt the promoter are suitable.

In a particularly preferred embodiment, nucleic acid sequences comprising the structural gene in question or upstream sequences are utilized for targeting heterologous recombination constructs. The use of homologous recombination to alter expression of endogenous genes is described in detail in U.S. Pat. No. 5,272,071, WO 91/09955, WO 93/09222, WO 96/29411, WO 95/31560, and WO 91/12650.

E) Use of Other Molecules.

Numerous other approaches can be taken to downregulate CYP24 activity. As indicated above, particularly using high throughput screening methods, literally thousands of compounds can be tested for ability to alter (e.g. downregulate) CYP24 activity. Any one or more of the compounds identified above or in such screening systems can be used to modulate CYP24 activity.

F) Administration of CYP24 Modulators.

The compounds that modulate (e.g. downregulate) CYP24 activity can be administered by a variety of methods including, but not limited to parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the CYP24 modulators (e.g. antibodies, antisense constructs, ribozymes, small organic molecules, etc.) when administered orally, must be protected from digestion. This is typically accomplished either by complexing the molecule(s) with a composition to render it resistant to acidic and enzymatic hydrolysis or by packaging the molecule(s) in an appropriately resistant carrier such as a liposome. Means of protecting agents from digestion are well known in the art.

The compositions for administration will commonly comprise a CYP24 modulator dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing modulators of CYP24 can be administered for therapeutic or prophylactic treatments. In therapeutic applications, compositions are administered to a patient suffering from a disease (e.g., an epithelial cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient.

VI. Kits for Use in Diagnostic and/or Prognostic Applications.

For use in diagnostic, research, and therapeutic applications suggested above, kits are also provided by the invention. In the diagnostic and research applications such kits may include any or all of the following: assay reagents, buffers, CYP24 specific and/or VDR specific nucleic acids or antibodies (e.g. full-size monoclonal or polyclonal antibodies, single chain antibodies (e.g., scFv), or other CYP24 or VDR binding molecules), and other hybridization probes and/or primers, and/or substrates for 25-hydroxyvitamin D3 24-hydroxylase. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Identification of CYP24 as a Driver Oncogene for Amplification at 20q13.2

This experiment describes genetic analysis of breast tumors that indicates selective amplification of CYP24. Selection for higher copy number of this gene during tumor evolution provides further evidence of the importance of the vitamin D pathway in tumor development in the breast.

We have used a new high resolution form of comparative genomic hybridization, array CGH, to obtain a high resolution, quantitative map of DNA copy number across a region of recurrent amplification at chromosome band 20q13.2. Array CGH, which was developed in our laboratories uses microarrays of DNA clones as the hybridization target so that its resolution is determined by the spacing of the target clones across a genomic region (FIG. 1). Thus, when contiguous clones make up the array, very high resolution copy number profiles can be obtained.

The unprecedented high dynamic range and quantitative accuracy of array CGH provides for the first time, the capability to very precisely map copy number profiles across an amplified region. In some tumors, copy number profiles show narrow peaks of amplification (~300 kb in FIG. 3). This information focuses attention on genes mapping to the region and indicates that they should be given highest priority for evaluation as candidate driver oncogenes. The application of high resolution array CGH across region A at chromosome band 20q13.2 in breast cancer revealed the existence of two subregions, A1 and A2 with distinct amplification behavior. Recently a candidate oncogene, ZNF217 (Collins et al., 1998) has been identified that maps to subregion A1 and is likely to be the driver gene for amplification of A1. Our attention is now focused on the gene CYP24 as the driver oncogene for region A2, because it maps to the narrow genomic interval most highly amplified in these tumors.

Figure 3:
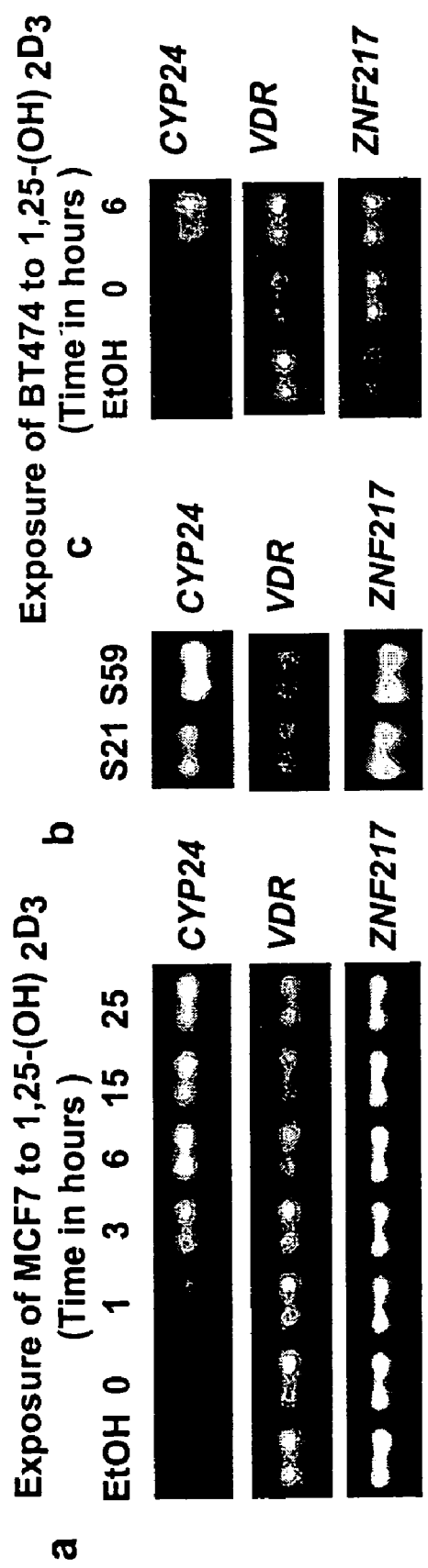
FIG. 3 illustrates expression of CYP24, VDR and ZNF217 genes in human breast cancer cell lines and tumors with and without induction by 1,25-dihydroxyvitamin $D_3$ evaluated by RT-PCR. (a) Time course of induction of CYP24 gene expression in MCF7 breast cancer lines incubated with $10^{-8}$ M 1,25-dihydroxyvitamin $D_3$ and vehicle control (ethanol, EtOH). (b) Gene expression in two breast cancer tumors, S21 and S59. (c) Gene expression in the BT474 cell line. Cells were incubated with $10^{-8}$ M 1,25-dihydroxyvitamin $D_3$, as described in (a).

Previously, CYP24 had been discounted as a candidate oncogene because it was not found to be transcribed in the breast cancer cell line, BT474 (Collins et al. (1998) *Proc. Natl. Acad. Sci. USA* 95: 8703-8708). However, re-evaluation of expression of CYP24 in cell lines and tumors was warranted because of its position at the peak of the copy number profile and because of the existing knowledge of its function. Therefore we examined expression levels of CYP24 and the vitamin D receptor (VDR), which controls CYP24 expression by RT-PCR using the primers listed in Table 1. This re-evaluation shows that these genes are expressed in breast cancer cell lines and tumors (FIG. 3). Expression of CYP24 and VDR was detected in MCF7 cells and higher levels of expression of CYP24 were induced when cells were treated with 1,25-dihydroxyvitamin-D3 (FIG. 3A). Furthermore, expression of CYP24 and VDR was detected in two breast tumors S21 and S59 (FIG. 3B). In BT474 however, CYP24 expression was not detected without addition of 1,25-dihydroxyvitamin-D3 to the culture medium (FIG. 3C). Only low level expression of VDR was found in this cell line, most likely accounting for the failure to detect expression of CYP24 in BT474 without addition of 1,25-dihydroxyvitamin-D3. These observations on BT474 illustrate the complexity of the analysis of CYP24 function and emphasize the importance of measuring VDR activity when evaluating the role of CYP24 in tumorigenesis.

TABLE 1

Primers used for assessing gene expression of CYP24 and VDR.

| Primer Name | Sequence | SEQ ID NO |
|---|---|---|
| CYP24 Forward | 5'-(AAT TAA CCC TCA CTA AAG GG) CAA ACC GTG GAA GGC CTA TC-3'* | 1 |
| CYP24 Reverse | 5'-(TAA TAC GAC TCA CTA TAG GGA G)T CTT CCC TTC CAG GAT CA-3'** | 2 |
| VDR.Forward | 5'-CTTCAGGCGAAGCATGAAGC-3'+ | 3 |
| VDR Reverse | 5'-CCTTCATCATGCCGATGTCC-3' | 4 |
| ZNF217 Forward | 5'-(AAT TAA CCC TCA CTA AAG GG) AGA GGG GTG AGT GAC AAG-3'* | 5 |
| ZNF217 Reverse | 5'-(TAA TAC GAC TCA CTA TAG GG) AGC TCG GAA TGG AAC AAC-3'ᵃ | 6 |

*T3 promoter shown in parentheses is included at the 5' end so that the amplified product can be used as a template for in vitro transcription to generate riboprobes for mRNA FISH.
**T7 promoter shown in parentheses is included at the 5' end so that the amplified product can be used as a template for in vitro transcription to generate riboprobes for mRNA FISH.
The reverse primer spans the second exon-exon junction, preventing amplification of genomic DNA. A 111 bp fragment is amplified.
+Spans the third exon-exon junction.
++A 134 bp PCR fragment is amplified.
ᵃA 265 bp PCR fragment is amplified.

Example 2

Expression Analysis Using Multi-Color Fluorescent In Situ Hybridization (mRNA FISH) on Tissue Sections In order to identify genes that are overexpressed in tumor compared to normal tissue, we have adapted our FISH protocols for visualizing transcription patterns in *C. elegans* (Albertson et al. (1995) pages 339-364 In *C. elegans: Modern Biological Analysis of an Organism*, vol. 48, H. F. Epstein and D. C. Shakes, eds. Academic Press, Inc; Birchall et al. (1995) *Nature Genet.* 11: 314-320) for use with formalin fixed paraffin embedded clinical specimens. Our approach involves the use of fluorescently labeled riboprobes that are synthesized by in vitro transcription. The DNA template for the transcription reaction is generated by amplification using gene specific primers in which the T3 or T7 phage promoter has been incorporated in the 5' end. Thus, subcloning of gene fragments to make probes can be avoided.

The hybridization signal was imaged with a confocal microscope, that reduces interference from tissue autofluorescence because of the narrow wavelength exciting light and the exclusion of out of focus fluorescence. The use of fluorescent probes, rather than radioactive probes has a number of advantages including, higher resolution, time saving, compatability with simultaneous immunohistochemistry (Chuang et al. (1996) *Cell*, 79: 1-20) and the possibility of measuring relative levels of expression of a number of genes simultaneously on a single tissue section (Albertson et al., 1995).

Example 3

Expression of CYP24 and VDR in Normal Mammary Cells

In the human, vitamin D receptors have been localized by immunohistochemistry to the luminal and alveolar epithelial cells of the normal breast and in breast tumor cells (Berger et al. (1987) *Cancer Res.* 47: 6793-6799; Colston et al. (1989) *Lancet*, 188-191). In this experiment, the expression profiles of the CYP24 and VDR genes during various stages of murine mammary gland development and involution are determined in order to identify the cell types and developmental stages in which these gene products function. These studies will provide the description of the normal expression of these genes, which are then compared to expression in murine breast tumor models and the CYP24 transgenic mouse to be developed as described below.

The expression analysis is carried out at both the transcript and protein levels. As described above gene specific probes for CYP24 and VDR mRNAs can be used to generate riboprobes for mRNA FISH. Antibodies specific for VDR are commercially available (Affinity BioReagents #PA1-711, MA1-710; Santa Cruz Biotechnology #sc-1008, sc-1009)

Immunohistochemistry and/or a combination of mRNA FISH and immunohistochemistry are used to localize the site of expression of particular genes and marker proteins specific for various cell types in the breast. Where possible, localization of expression of CYP24 and/or VDR and the cell type specific markers is carried out simultaneously on the same tissue sections using multiple distinguishable fluorochromes on the probes for the genes and marker proteins.

Development of the rodent breast has been described (see, e.g., Medina (1996) *J. Mamm. Gland Biol. Neopl.* 1: 5-19) and begins by arborization of the ductal system throughout the mammary fat pad at 4-8 weeks of age. The terminal end-buds, located at the leading edge of the invading ducts contain proliferating cells. At the time of pregnancy, further arborization of the ductal system takes place by elaboration of tertiary end-buds from the sides of the existing ductal tree. Terminal differentiation of the gland takes place during lactation when the milk proteins, lactoglobulin and whey acidic protein are synthesized. Involution of the lactating mammary gland involves extensive apoptosis and occurs during 4-6 weeks following weaning.

Experimental Design.

Expression of CYP24 and VDR is determined by in situ staining of tissue sections using mRNA FISH or gene specific antibodies. Tissue blocks are prepared following in vivo perfusion and fixation of the mice. Mammary glands are harvested from mice at: (a) the beginning and end of breast ductal arborization (at 3-4 weeks and at 8 weeks, respectively), (b) at early, intermediate and late stages of pregnancy (at 4, 8, 13, and 18 days post coitus), (c) during lactation, and (d) during early and late breast involution (at 4 and 8 weeks after elective weaning). Prior to sacrifice, all mice are injected with 5-bromo-deoxyuridine (BrdU) for immunohistochemical detection of S-phase cells using monoclonal BrdU antibody (Arbeit, et al., 1994). Immunohistochemical staining of keratin intermediate filament proteins is used to distinguish the basal (keratin-14) and luminal cells (keratin-6) of the ducts (Antibodies, BabCo # prb-155p, -169p). The early and late stages of involution is identified by using the TUNEL assay for apoptosis (Naik et al. (1996) Genes Dev. 10: 2106-2166).

Methods.

Specimen Preparation.

Mice are injected i.p. with 100 mg/kg BrdU 2 hrs prior to sacrifice. The mice are weighed and anestheized with 37.5 mg/kg of a 0.25% Avertin solution and perfused with a 3.75% solution of freshly prepared paraformaldehyde. Tissues are removed, post-fixed overnight in 3.75% paraformaldehyde at 4° C. and then embedded in paraffin. Sections (~6 µm thickness) are de-waxed in xylene, taken through a graded series of ethanols and then incubated with 5-15 µg/ml of proteinase K at 37° C. for 15 min., depending on the application. Following protease treatment the specimens are post-fixed in 1% paraformaldehyde for 20 min. at room temperature, rinsed and then dehydrated.

mRNA FISH.

Specimens are pre-hybridized in hybridization buffer (50-70% formamide, 5×SSC, 0.1% SDS, 0.1% Tween 20, 100 µg/ml tRNA, 10% dextran sulfate) at 37° C. for 2 hrs. The pre-hybridization solution is removed and the fluorescently labeled riboprobe (Albertson et al. (1995) pages 339-364 In *C. elegans: Modern Biological Analysis of an Organism*, vol. 48, H. F. Epstein and D. C. Shakes, eds. Academic Press, Inc) are applied to the specimen in hybridization buffer. Hybridization is carried out overnight at 37-50° C. depending on the length and GC content of the probe.

Immunohistochemistry.

Processing of sections varies slightly depending on the antibody, but will use standard methods for indirect detection (e.g. Albertson (1984) *Develop. Biol.* 101: 61-72).

S Phase Analysis.

After immunohistochemical staining for BrdU positive cells, the BrdU labeling index is determined by counting 1000 nuclei in sequential 20× fields.

Apoptosis.

The TUNEL assay is carried out using fluorescent detection of terminal transferase activity according to the manufacturer's directions (Oncor # S7110, Gaiterburg, Md.).

Data Collection and Analysis.

Expression profiles of CYP24 and VDR in mammary tissue includes enumeration of specific cell types, developmental stage-specific expression patterns and relative levels of expression. Expression of cell specific marker proteins is used to confirm assignment of CYP24 and VDR expression in particular cells and developmental stages. The basal and luminal cells of the ducts are distinguished by their expression of particular keratins and proliferating terminal end-buds will be identified by BrdU incorporation. Involuting cells are identified as TUNEL positive cells. The relative levels of expression of CYP24 and VDR mRNA at the different developmental stages are measured relative to a ribosomal probe hybridized to the same tissue sections.

Example 4

Expression of CYP24 in the Established Murine Breast Cancer Model, MMTV-ERBB2 Transgenic Mouse We have documented the expression of CYP24 and VDR in human breast tumor specimens (FIG. 3) and will continue to survey expression of these genes in normal and tumor tissue from human breast tumor specimens. Here, we will investigate the expression of CYP24 and VDR during breast carcinogenesis in an established transgenic mouse model of breast cancer, in which the ERBB2 oncogene is expressed in mammary tissue under the control of the mouse mammary tumor virus promoter (JAX Mice, MMTVneu Erbb2, #002376). These mice first develop focal tumors in hyperplastic, dysplastic mammary glands at ~4 months (Guy et al., 1992). The study of transgenic mouse models of breast carcinogenesis offers the opportunity to investigate the potential role of these genes in certain aspects of tumorigenesis that cannot be studied by analysis of patient material. In particular, mouse models offer access to premalignant stages generally not available from human specimens. Furthermore, murine tumor models allow the role of particular genes in tumorigenesis to be assessed in tumors induced in a defined genetic background (e.g. tumors induced by overexpression of ERBB2, cyclin D1 or loss of p53).

Experimental Design.

Transgenic mice of 2, 4, 6 and 10-12 months are studied to encompass time points of early and late tumor development. Two hours prior to sacrifice, BrdU is injected intra-peritoneally to measure S-phase kinetics. Tissues are harvested and processed for mRNA FISH, and expression of keratins-14 and -6, and the HER2-neu transgene are determined, using antibodies as in Example 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting a breast cancer marker in a human, said method comprising:
   (i) providing a biological sample from said human;
   (ii) detecting the level of CYP24 nucleic acid or CYP24 protein, within said biological sample, wherein said CYP24 nucleic acid or CYP24 protein is a nucleic acid or protein encoded by a vitamin D 24 hydroxylase (CYP24) gene that can be amplified using amplification primers, wherein one primer comprises SEQ ID NO: 1 and another primer comprises SEQ ID NO: 2; and
   (iii) comparing said level of CYP24 nucleic acid or CYP24 protein with a level of CYP24 nucleic acid or CYP24 protein in a control sample taken from a normal, cancer-free tissue; wherein an increased level of CYP24 nucleic acid or CYP24 protein in said biological sample compared to the level of CYP24 nucleic acid or CYP24 protein in said control sample indicates the presence of said breast cancer marker in said human.

2. The method of claim 1, wherein said level of CYP24 nucleic acid is detected by determining the copy number of CYP24 genes in the cells of said biological sample.

3. The method of claim 2, wherein said copy number is measured using Comparative Genomic Hybridization (CGH).

4. The method of claim 2, wherein said copy number is determined by hybridization to an array of nucleic acid probes.

5. The method of claim 3, wherein said Comparative Genomic Hybridization is performed on an array.

6. The method of claim 1, wherein said level of CYP24 nucleic acid is detected by measuring the level of CYP24 mRNA in said biological sample, wherein an increased level of CYP24 mRNA in said sample compared to CYP24 mRNA in said control sample indicates the presence of said breast cancer marker.

7. The method of claim 6, wherein said level of CYP24 mRNA is measured in said biological sample and said control sample at the same vitamin D receptor activity or the CYP24 mRNA levels are normalized to the level of vitamin D receptor activity in the sample and control.

8. The method of claim 6, wherein said level of CYP24 mRNA is measured by hybridization to one or more probes on an array.

9. The method of claim 1, wherein said level of CYP24 nucleic acid or CYP24 protein is detected by measuring the level of CYP24 protein in said biological sample, wherein an increased level of CYP24 protein in said sample as compared to CYP24 protein in said control sample indicates the presence of said breast cancer marker.

10. The method of claim 9, wherein the level of CYP24 protein is measured in the biological sample and the control sample at the same vitamin D receptor activity or the protein levels are normalized to the level of vitamin D receptor activity in the sample and control.

11. The method of claim 1, wherein said level of CYP24 nucleic acid or CYP24 protein is detected by measuring the level of 25-hydroxyvitamin D3 24-hydroxylase enzyme activity in said biological sample, wherein an increased level of 25-hydroxyvitamin D3 24-hydroxylase enzyme activity in said sample as compared to 25-hydroxyvitamin D3 24-hydroxylase enzyme activity in said control sample indicates the presence of said breast cancer marker.

12. The method of claim 11, wherein said level of 25-hydroxyvitamin D3 24-hydroxylase activity is measured in said biological sample and said control sample at the same vitamin D receptor activity or the activity levels are normalized to the level of vitamin D receptor activity in the sample and control.

13. The method of claim 1, wherein said biological sample is selected from the group consisting of excised tissue, whole blood, serum, plasma, buccal scrape, saliva, cerebrospinal fluid, and urine.

14. The method of claim 1, wherein the difference between said increased level of CYP24 nucleic acid or CYP24 protein in said biological sample and the level of CYP24 nucleic acid or CYP24 protein in said control sample is a statistically significant difference at the 95 percent or greater confidence level.

15. The method of claim 1, wherein said increased level of CYP24 nucleic acid or CYP24 protein in said biological sample is at least about 2-fold greater than the level of CYP24 nucleic acid or CYP24 protein in said control sample.

16. The method of claim 1, wherein said increased level of CYP24 nucleic acid or CYP24 protein in said biological sample is at least about 4-fold greater than said level of CYP24 nucleic acid or CYP24 protein in said control sample.

17. The method of claim 9, wherein the level of CYP24 protein is measured by immunoassay using at least one antibody that specifically binds to CYP24 protein.

18. The method of claim 1, wherein said human is suspected of having breast cancer.

19. The method of claim 1, wherein said breast cancer marker is found to be present in said human, and said method additionally comprises subjecting said human to an adjuvant cancer therapy.

* * * * *

SEQUENCE LISTING

<160> NUMBER OF SEQ ID NOS: 6

<210> SEQ ID NO 1
<211> LENGTH: 40
<212> TYPE: DNA
<213> ORGANISM: Artificial Sequence
<220> FEATURE:
<221> NAME/KEY: promoter
<222> LOCATION: (1)..(20)
<223> OTHER INFORMATION: T3 promoter

```
<220> FEATURE:
<223> OTHER INFORMATION: Description of Artificial Sequence: primer

<400> SEQUENCE: 1
aattaaccct cactaaaggg caaaccgtgg aaggcctatc                              40

<210> SEQ ID NO 2
<211> LENGTH: 40
<212> TYPE: DNA
<213> ORGANISM: Artificial Sequence
<220> FEATURE:
<221> NAME/KEY: promoter
<222> LOCATION: (1)..(22)
<223> OTHER INFORMATION: T7 promoter
<220> FEATURE:
<223> OTHER INFORMATION: Description of Artificial Sequence: primer

<400> SEQUENCE: 2
taatacgact cactataggg agtcttccct tccaggatca                              40

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
cttcaggcga agcatgaagc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
ccttcatcat gccgatgtcc                                                   20

<210> SEQ ID NO 5
<211> LENGTH: 38
<212> TYPE: DNA
<213> ORGANISM: Artificial Sequence
<220> FEATURE:
<221> NAME/KEY: promoter
<222> LOCATION: (1)..(20)
<223> OTHER INFORMATION: T3 promoter
<220> FEATURE:
<223> OTHER INFORMATION: Description of Artificial Sequence: primer

<400> SEQUENCE: 5
aattaaccct cactaaaggg agagggtga gtgacaag                                 38

<210> SEQ ID NO 6
<211> LENGTH: 38
<212> TYPE: DNA
<213> ORGANISM: Artificial Sequence
<220> FEATURE:
<221> NAME/KEY: promoter
<222> LOCATION: (1)..(20)
<220> FEATURE:
<223> OTHER INFORMATION: Description of Artificial Sequence: primer

<400> SEQUENCE: 6
taatacgact cactataggg agctcggaat ggaacaac                                38
```